United States Patent [19]
Grainger et al.

[11] 4,369,311
[45] Jan. 18, 1983

[54] METHOD OF PREPARATION OF CYCLIC NITRILE SULFITES

[75] Inventors: James L. Grainger, College Park, Ga.; Kent D. Campbell, Concord, Calif.

[73] Assignee: The Dow Chemical Company, Midland, Mich.

[21] Appl. No.: 301,492

[22] Filed: Sep. 14, 1981

[51] Int. Cl.³ .................. C07D 419/10; C07D 419/14; C07D 291/04
[52] U.S. Cl. .................................... 542/443; 542/437; 548/122
[58] Field of Search ................ 548/122; 542/433, 443, 542/437

[56] References Cited

U.S. PATENT DOCUMENTS

| | | | |
|---|---|---|---|
| 3,238,220 | 3/1966 | Boshagen | 548/122 |
| 3,423,449 | 1/1969 | Burk, Jr. et al. | 548/122 |
| 3,649,636 | 3/1972 | Burk, Jr. et al. | 548/122 |
| 3,979,401 | 9/1976 | Burk, Jr. et al. | 548/122 |

OTHER PUBLICATIONS

Bodrikov et al., Chem. Abs. 90:87359d (1979).

*Primary Examiner*—Mary C. Lee
*Attorney, Agent, or Firm*—Paul D. Hayhurst

[57] ABSTRACT

Cyclic nitrile sulfites are prepared by reacting the corresponding amide with sulfur dioxide in a solvent and in the presence of an oxidizing agent, e.g., lead tetraacetate, and a catalyst, e.g., triethylamine.

10 Claims, No Drawings

METHOD OF PREPARATION OF CYCLIC NITRILE SULFITES

BACKGROUND OF THE INVENTION

This invention relates to a new method for the preparation of cyclic nitrile sulfites.

Cyclic nitrile sulfites are useful in that they may be thermally decomposed to form the corresponding isocyanates. Cyclic nitrile sulfites have been prepared in the past by reacting an appropriate corresponding hydroxamic acid with thionyl chloride, and that reaction is described in several United States patents including U.S. Pat. Nos. 3,979,401; 3,763,175; 3,423,447 and others.

SUMMARY OF THE INVENTION

The present invention is a new method for the preparation of cyclic nitrile sulfites. These compounds are prepared by contacting an amide with sulfur dioxide and an oxidizing agent in the presence of a catalyst under conditions sufficient to produce the corresponding cyclic nitrile sulfite. Surprisingly, the method of the present invention enables the production of cyclic nitrile sulfites in a single step using amides as a starting material, thereby eliminating the need to convert amides to the hydroxamic acids used in the prior art method.

The nitrile sulfites produced by the present invention are valuable intermediates for the preparation of highly desired chemicals. For example, these compounds can be thermally decomposed to yield isocyanates. Isocyanates, such as diisocyanates, are widely used in the preparation of high molecular weight polymers. For example, polyurethanes are commonly prepared by the reaction of diisocyanates and polybasic alcohols such as the glycols. Details of the thermal decomposition of nitrile sulfites to produce isocyanates are given in U.S. Pat. Nos. 3,979,401.

DETAILED DESCRIPTION OF THE INVENTION

Generally, the amide reactants of this invention are characterized by having at least one reactive amide moiety, $-CONH_2$, bonded to an aromatic hydrocarbon radical.

Preferred amide reactants are represented by the formula:

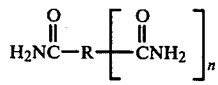

wherein R is an aromatic hydrocarbon radical and n is from 0 to 3. Most preferably, n is 1, i.e., diamides are most preferred.

The aromatic hydrocarbon radicals of the present invention may be mono- or polyvalent and may have from 1 to about 30 carbon atoms. Preferred aromatic radicals contain from about 6 to about 18 aromatic carbon atoms and may have from 1 to 3 aromatic rings. These radicals may be mixed aromatic-aliphatic groups, e.g., alkyl phenyl, aralkyl, alkaryl, and others. The radicals may be saturated or unsaturated and may contain inert substituents which would not be affected under the oxidative cyclization conditions of the reactions of the present invention. Examples of these substituents include $-NO_2$, $-Br$, $-Cl$, $-F$, $-OCH_3$ and the like.

An especially preferred aromatic hydrocarbon radical is represented by the following formula:

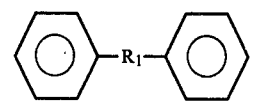

wherein $R_1$ is arylene or $C_1$ to $C_3$ alkylene. The most preferred aromatic radical is diphenyl methane; the corresponding nitrile sulfite product is diphenylmethane-di(nitrile sulfite) or 5,5'-(methylene di-4,1-phenylene)bis(1,3,2,4-dioxathiazole 2-oxide). When the aromatic radical contains a single aromatic ring and two reactive amide moieties, the amide groups are preferably in a non-ortho position with respect to each other on the aromatic ring.

The oxidizing agent of this invention can be chosen from a number of known mild oxidizing agents, including, for example, stannic (tin IV) or plumbic (lead IV) acetate. Lead tetraacetate is the preferred oxidizing agent. The oxidizing agent must be strong enough to oxidize the reactive amide moieties of the amide reactant, but should not be strong enough to oxidize the $SO_2$ in the reaction mixture to such an extent that the reaction would be adversely affected. Additionally, the oxidizing agent should be chosen so that neither water nor strong acids are formed when the oxidizing agent dissociates in the reaction mixture. Typically, from about 1 to about 4 moles of oxidizing agent are employed for each mole of amide moiety. Preferably this range is from about 1 to about 2 moles of oxidizing agent per mole of amide moiety.

The reaction is conducted in the presence of an amount of sulfur dioxide which is sufficient to induce cyclic nitrile sulfite formation, typically this amount ranges to from about 10 to about 100 moles of sulfur dioxide for each mole of amide moiety. Preferably from about 30 to about 50 moles of sulfur dioxide are employed per mole of amide moiety. Typically, the sulfur dioxide will be condensed into the reaction mixture and will be dissolved therein, but any method of introducing sulfur dioxide to the reaction mixture which results in the desired reaction is acceptable.

A catalyst is employed to advantage in the method of this invention. The catalysts of this invention are characterized by an alkaline functionality and their ability to shorten the time required to complete the cyclization reactions of this invention while maintaining or improving upon the yield of the corresponding non-catalyzed reaction. Examples of said catalysts include organic tertiary amines including pyridine and trialkylamines such as trimethylamine, triethylamine, and tri-(n-propyl)-amine. Triethylamine is the preferred catalyst. Generally, the initial reaction mixture may contain from about 0.1 to about 5 moles of the selected catalyst per mole of amide moiety. The reaction mixture preferably will have from about 1 to about 2 moles of catalyst per mole of amide moiety.

The temperature for conducting the reaction of the present invention may vary from about 0° C. to about 100° C. but in any case must be below the decomposition temperature of the desired nitrile sulfite product. Preferably, the reaction will be conducted between about 10° C. and about 25° C. Ordinarily, the reaction will proceed readily at atmospheric pressure or higher, but subatmospheric pressures can be employed if desired.

A solvent is advantageously employed in the method of this invention. The solvent functions to solubilize the reactants and to activate the oxidizing agent. The amount of solvent to be employed is indicated by practical considerations, but can range from about 10 to about 300 moles of solvent per mole of amide moiety. Typical solvents include dimethylformamide, hexamethylphosphoramide and 1-methyl-2-pyrrolidinone. Anhydrous dimethylformamide is the preferred solvent. It should be noted that the solvent employed must not contain reactive amide (—CONH$_2$) moieties, but it may contain substituted amide moieties as does dimethylformamide.

For the purposes of this invention the term mole(s) of amide moiety refers only to amide moieties of the amide reactant and does not include amide moieties of the solvent.

The cyclic nitrile sulfite product can be recovered from the reaction mixture by any desirable means. For example, recovery may be effected by first adding ice water to the mixture causing the more water-insoluble products to precipitate, or by extraction of the product from the aqueous solution using a suitable organic solvent.

The cyclic nitrile sulfite products of the present invention are characterized by having at least one cyclic nitrile sulfite group. For the purposes of this invention, a cyclic nitrile sulfite group is represented by the following formula I:

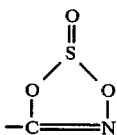

Preferred cyclic nitrile sulfite products produced by the method of the present invention are represented by formula I:

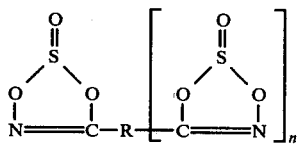

wherein R is an aromatic hydrocarbon radical and n is from 0 to 3. Most preferably n is 1.

The following example is given to illustrate the invention and should not be construed as limiting its scope. All percentages in the example are by weight unless otherwise indicated.

EXAMPLE 1

In a 100 ml, 3-neck, round-bottomed flask which is immersed in a methanol/ice bath and which is equipped with a dry ice acetone condenser, magnetic stirrer and a thermometer, 3.5 mmoles of 4,4'-methylene bis(benzamide) is dissolved in 40 ml of anhydrous dimethylformamide. To this mixture, 0.112 mole of gaseous SO$_2$ is condensed to the liquid phase and added to the flask while the temperature of the mixture is maintained at $-15°$ C.$\pm 4°$ C. at ambient pressure. Then 0.008 mole of freshly prepared lead tetraacetate is added under a positive pressure of SO$_2$. The solution remains light yellow. Then 1.5 ml of triethylamine is added to catalyze the reaction and the temperature is allowed to rise to 10° C. where a color change to a dark translucent hue indicates reaction. Infrared analysis of the reaction mixture after 30 minutes of reaction shows no N-H stretch characteristic of amides but shows significant absorption in the 7.97 micron region which is characteristic of cyclic nitrile sulfites. The reaction is allowed to proceed at 10° C.-15° C. for an additional hour.

The product mixture is added to 100 ml of ice water with the immediate formation of a light brown precipitate. This solid is filtered away from the solution and is found to contain a small amount of diisocyanate (N=C=O absorption in IR at 2220 cm$^{-1}$) and product, but is predominantly lead salts. The product is extracted from the filtrate solution using CH$_2$Cl$_2$, dried over MgSO$_4$ and solvent stripped off to yield 0.80 g of a light yellow oil which solidifies upon standing. The product is identified by the strong absorption at 1255 cm$^{-1}$ (7.97 μm) which is characteristic of this type of compound.

Heating the solid product at 130° C. gives 1,1'-methylene bis(4-isocyanatobenzene) and gaseous SO$_2$ with a diisocyanate yield of approximately 70 percent.

What is clamed is:

1. A process comprising contacting in a solvent an amide reactant having bonded to an aromatic hydrocarbon radical at least one reactive amide moiety, —CONH$_2$, with sulfur dioxide in the presence of an oxidizing agent and a catalyst under conditions sufficient to form a cyclic nitrile sulfite.

2. The process of claim 1 wherein the cyclic nitrile sulfite corresponds to formula I:

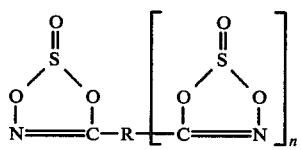

wherein n is from 0 to 3 and R is a mono- or polyvalent aromatic, including mixed aliphatic-aromatic, hydrocarbon radical which may contain inert substituents which would not be affected under the aforementioned reaction conditions, said substituents being chosen from halo, —NO$_2$, and lower alkoxy.

3. The process of claim 2 wherein R is selected from the group consisting of aromatic hydrocarbons having from 6 up to 18 aromatic carbon atoms and having 1 to 3 aromatic rings, and mixed aliphatic-aromatic hydrocarbons having from 1 to 30 carbon atoms.

4. The process of claim 3 wherein n is 1 to 3, R is aromatic or of the formula:

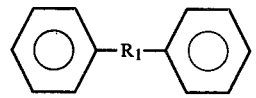

wherein R$_1$ is arylene or C$_1$ to C$_3$ alkylene.

5. The process of claim 4 wherein n is 1.

6. The process of claim 5 wherein R$_1$ is methylene or propylidene.

7. The process of claim 6 wherein the oxidizing agent is lead tetraacetate, the catalyst is triethylamine, and the solvent is anhydrous dimethylformamide.

8. The method of claim 7 wherein the temperature is up to about 25° C.

9. The process of claim 8 wherein R$_1$ is propylidene.

10. The process of claim 8 wherein R$_1$ is methylene.

* * * * *